United States Patent
Yamazaki

(10) Patent No.: US 8,480,571 B2
(45) Date of Patent: Jul. 9, 2013

(54) ENDOSCOPIC DEVICE

(75) Inventor: Kenji Yamazaki, Hino (JP)

(73) Assignee: Olympus Medical Systems Corp., Tokyo (JP)

(*) Notice: Subject to any disclaimer, the term of this patent is extended or adjusted under 35 U.S.C. 154(b) by 1364 days.

(21) Appl. No.: 12/190,235

(22) Filed: Aug. 12, 2008

(65) Prior Publication Data

US 2008/0306343 A1    Dec. 11, 2008

Related U.S. Application Data

(63) Continuation of application No. PCT/JP2006/324680, filed on Dec. 11, 2006.

(30) Foreign Application Priority Data

Mar. 3, 2006    (JP) .................................. 2006-058712

(51) Int. Cl.
    *A61B 1/06*    (2006.01)
(52) U.S. Cl.
    USPC ......................................... 600/178; 600/180
(58) Field of Classification Search
    USPC ............ 600/109, 160, 178, 180, 181; 362/574
    See application file for complete search history.

(56) References Cited

U.S. PATENT DOCUMENTS

| 2004/0122291 A1* | 6/2004 | Takahashi ..................... 600/180 |
| 2005/0117028 A1 | 6/2005 | Imaizumi et al. |

FOREIGN PATENT DOCUMENTS

| EP | 1 527 730 A1 | 5/2005 |
| JP | 63-264717 | 11/1988 |
| JP | 07-136107 | 5/1995 |
| JP | 2002-095635 | 4/2002 |
| JP | 2005-131129 | 5/2005 |

* cited by examiner

*Primary Examiner* — Philip R Smith
(74) *Attorney, Agent, or Firm* — Scully, Scott, Murphy & Presser, P.C.

(57) ABSTRACT

An endoscopic device of the present invention comprises: an endoscope having an image pickup unit that outputs a picked up an image of a subject as an image pickup signal; an image pickup signal amplification unit; a light source unit; a light intensity control unit that controls an amount of light; a spectral unit that penetrates light in a band based on predetermined characteristics; a brightness control unit that controls a brightness of an image displayed on a display unit; and a mode switching unit that switches a first mode for emitting first illumination light and a second mode for emitting second illumination light having a band narrower than the first illumination light, wherein the brightness control unit controls the light intensity control unit and then controls the image pickup signal amplification unit in the second mode.

4 Claims, 10 Drawing Sheets

ENDOSCOPIC DEVICE

CROSS REFERENCE TO RELATED APPLICATION

This application is a continuation application of PCT/JP2006/324680 filed on Dec. 11, 2006 and claims benefit of Japanese Application No. 2006-058712 filed in Japan on Mar. 3, 2006, the entire contents of which are incorporated herein by this reference.

BACKGROUND OF THE INVENTION

1. Field of the Invention

The present invention relates to an endoscopic device, and more particularly, to an endoscopic device having means for controlling the brightness of an image generated based on an image pickup signal outputted from an endoscope.

2. Description of the Related Art

An endoscopic device having an endoscope, a light source device, and the like has been conventionally widely used in the medical and other fields. Examples of generally known observations using the endoscopic device in the medical field include a normal observation of directing white light to a subject in a living body and then picking up an image of the subject substantially similar to visual observation and a narrow band imaging (NBI) of directing a narrow-band light to the subject, the light having a band narrower than the illumination light in the normal observation, to observe the subject, thereby allowing to pick up an image of a blood vessel of a superficial portion of the mucous membrane in the living body and the like, with an excellent contrast as compared to the normal observation.

With narrowing down of the band, the narrow-band light used in the narrow band imaging is emitted to a subject in a state with less light intensity compared to the illumination light used in the normal observation. Therefore, in the narrow band imaging, a control is necessary for amplifying and adjusting the brightness of the image based on the image of a subject picked up by the endoscope. Endoscopic devices that perform the above control are proposed, for example, in Japanese Patent Application Laid-Open Publication No. 07-136107 and in Japanese Patent Application Laid-Open Publication No. 2002-095635.

Even when an image with a desired brightness cannot be obtained with control to the light source device because the light intensity adjustment of the light control circuit is out of the range, the endoscopic device proposed in Japanese Patent Application Laid-Open Publication No. 07-136107 is configured to be able to obtain an image with a desired brightness by applying the gain adjustment of a video signal to a video processor.

The endoscopic device proposed in Japanese Patent Application Laid-Open Publication No. 2002-095635 is configured to be able to obtain an image adjusted to include an appropriate S/N in the narrow band imaging by increasing or decreasing the voltage level of the driving voltage of the lamp in accordance with the timing of the emission of the illumination light in each band included in the narrow-band light.

SUMMARY OF THE INVENTION

A first endoscopic device of the present invention comprises: an endoscope having image pickup unit for picking up an image of a subject and outputting the picked up image of the subject as an image pickup signal; image pickup signal amplification unit for amplifying the image pickup signal; light source unit for emitting first illumination light having at least a visible region band to the subject; light intensity control unit for controlling an amount of light emitted from the light source unit; spectral unit, having predetermined spectral characteristics, for penetrating a light in a band based on the predetermined spectral characteristics among the lights emitted from the light source unit when arranged on an optical path of the light source unit; brightness control unit for controlling a brightness of an image generated based on the image pickup signal and displayed on display unit; and mode switching unit for switching a first mode in which the spectral unit is removed from the optical path of the light source unit to emit the first illumination light to the subject and a second mode in which the spectral unit is arranged on the optical path of the light source unit to emit the second illumination light having a band narrower than the first illumination light to the subject, wherein the brightness control unit controls the light intensity control unit and then controls the image pickup signal amplification unit in the second mode.

In a second endoscopic device of the present invention according to the first endoscopic device, the light intensity control unit comprises: aperture unit arranged on the optical path of the light source unit; and light source drive unit for supplying a drive current to the light source unit.

In a third endoscopic device of the present invention according to the second endoscopic device, the brightness control unit executes control to the image pickup signal amplification unit, the aperture unit, and the light source drive unit in the first mode and the second mode in predetermined orders respectively.

In a fourth endoscopic device of the present invention according to the third endoscopic device, the brightness control unit controls the light source drive unit and then controls the image pickup signal amplification unit in the second mode.

In a fifth endoscopic device of the present invention according to the fourth endoscopic device, the brightness control unit further controls the aperture unit and then controls the light source drive unit in the second mode.

In a sixth endoscopic device of the present invention according to the fourth or fifth endoscopic device, the brightness control unit further controls the aperture unit and then controls the image pickup signal amplification unit in the first mode.

In a seventh endoscopic device of the present invention according to the fourth to sixth endoscopic devices, the brightness control unit detects the brightness of the image generated based on the image pickup signal and executes a predetermined control to the light source drive unit for changing the drive current supplied to the light source unit in stages based on the detection result in the second mode.

In an eighth endoscopic device of the present invention according to the seventh endoscopic device, the predetermined control is a control for changing a duty ratio of drive currents supplied to the light source unit by the light source drive unit.

In a ninth endoscopic device of the present invention according to the seventh or eighth endoscopic device, the predetermined control comprises: a first control executed immediately after the endoscopic device has switched from the first mode to the second mode; a second control executed after the first control and after the aperture unit has fully opened an aperture; and a third control executed after the second control.

DESCRIPTION OF THE PREFERRED EMBODIMENT(S)

Figure 1:
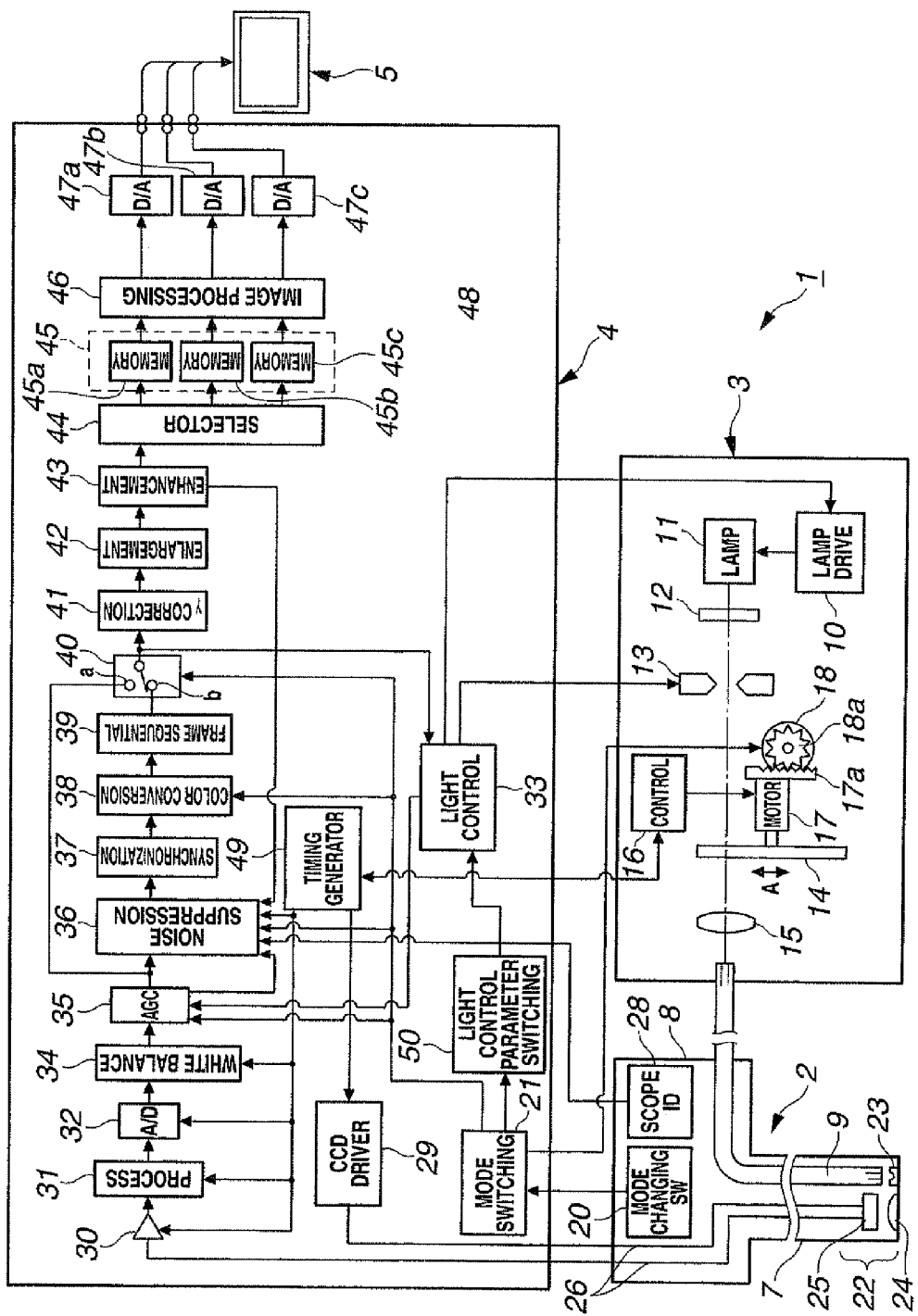
FIG. 1 is a diagram showing one example of a configuration of main parts in an endoscopic device of the present embodiment.
Figure 2:
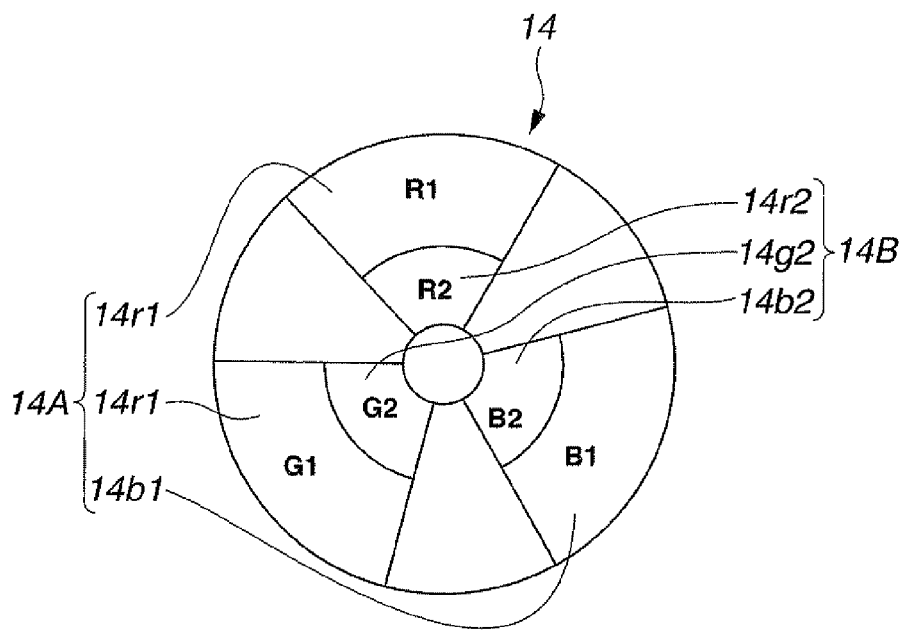
FIG. 2 is a diagram showing one example of a configuration of a rotating filter arranged on a light source device in the endoscopic device of the present embodiment.
Figure 3:
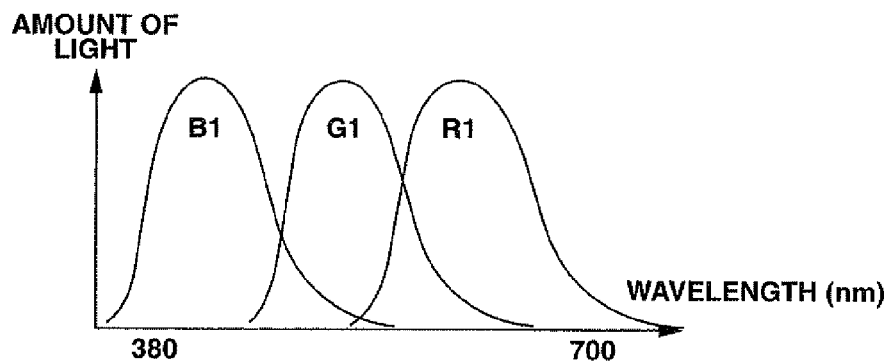
FIG. 3 is a diagram showing spectral characteristics of a filter used by the light source device for directing illumination light for normal observation in the endoscopic device of the present embodiment.
Figure 4:
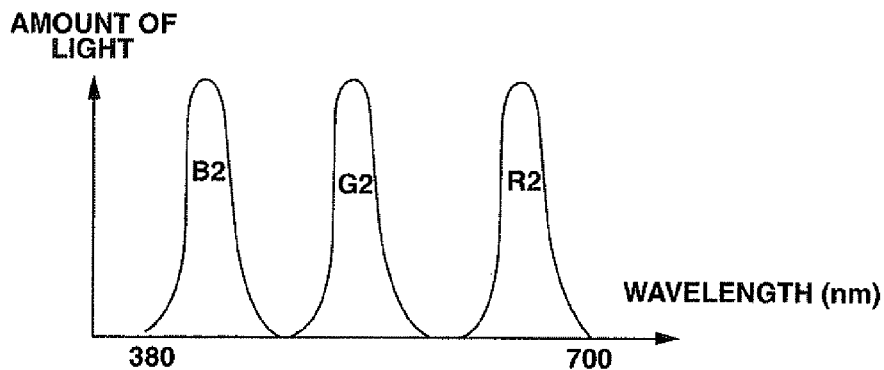
FIG. 4 is a diagram showing spectral characteristics of a filter used by the light source device for directing illumination light for narrow band imaging in the endoscopic device of the present embodiment.
Figure 5:
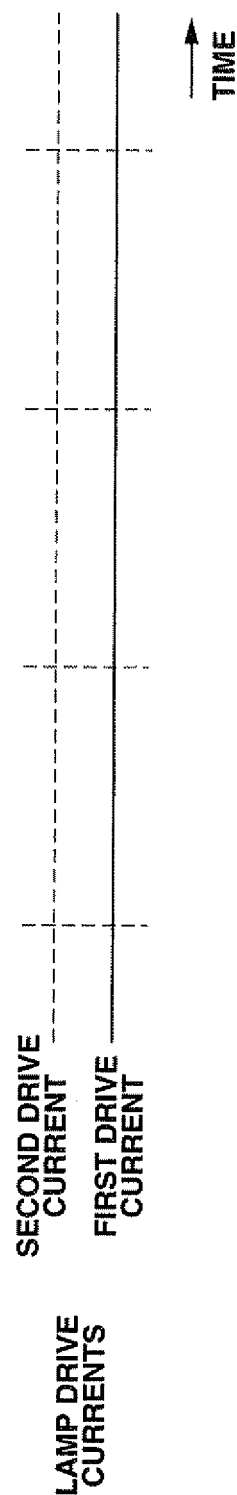
FIG. 5 is a diagram showing a state of a drive current supplied to a lamp when the endoscopic device of the present embodiment is in a normal observation mode.
Figure 6:
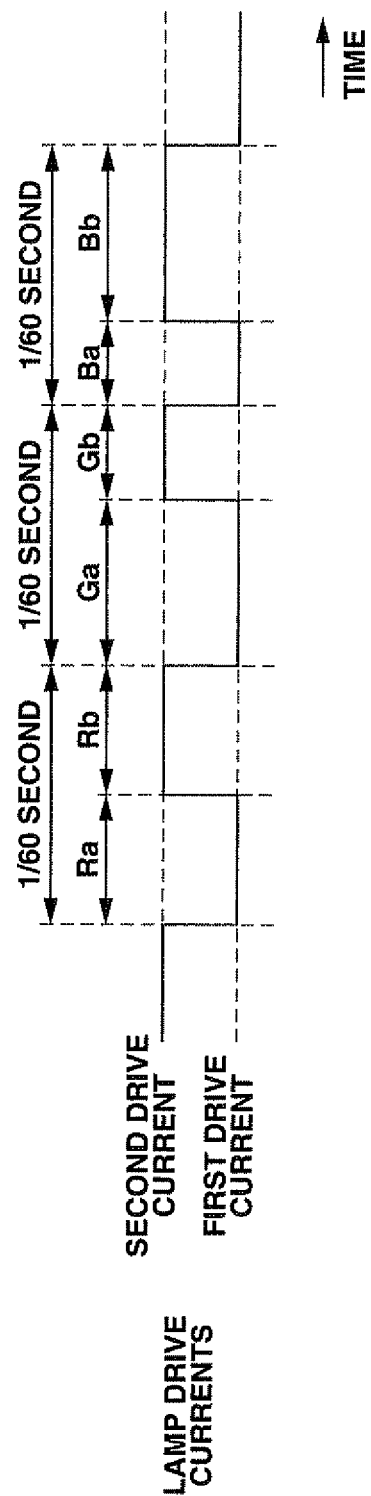
FIG. 6 is a diagram showing a state of a drive current supplied to the lamp in a first drive current control performed when the endoscopic device of the present embodiment is in a narrow band imaging mode.
Figure 7:
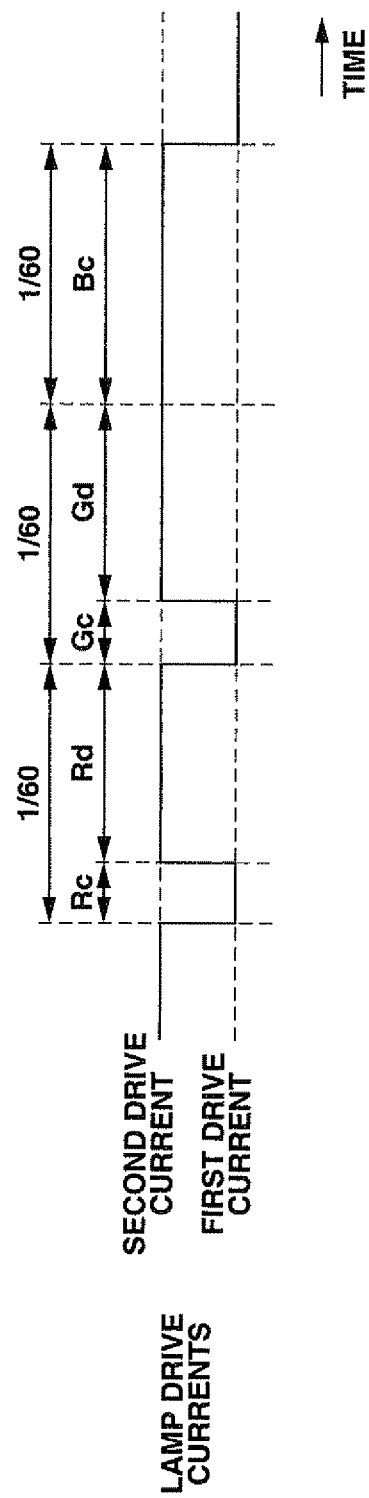
FIG. 7 is a diagram showing a state of a drive current supplied to the lamp in a second drive current control performed when the endoscopic device of the present embodiment is in the narrow band imaging mode.
Figure 8:
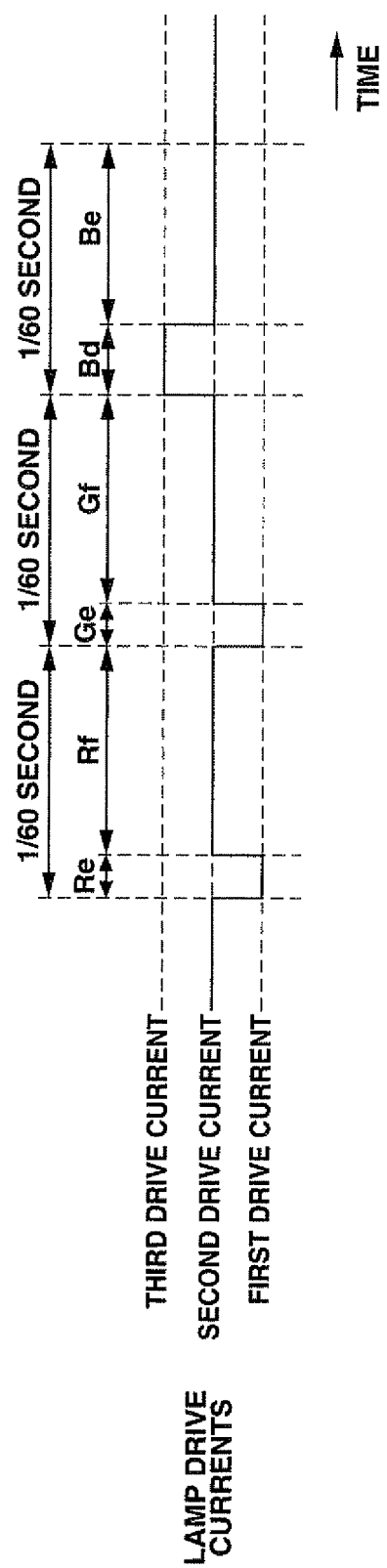
FIG. 8 is a diagram showing a state of a drive current supplied to the lamp in a third drive current control performed when the endoscopic device of the present embodiment is in the narrow band imaging mode.
Figure 9:
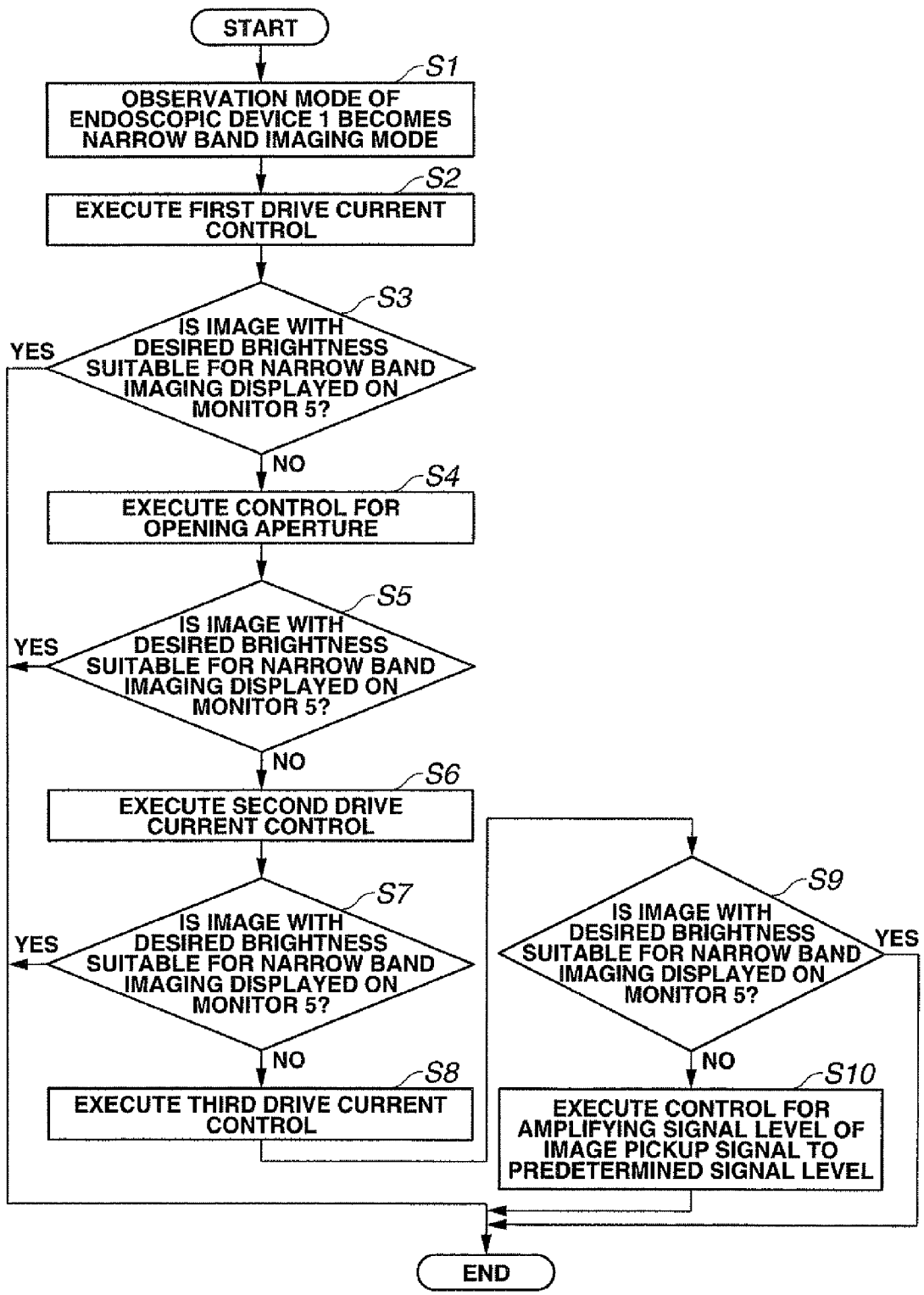
FIG. 9 is a diagram showing one example of a process executed when the endoscopic device of the present embodiment is in the narrow band imaging mode.
Figure 10:
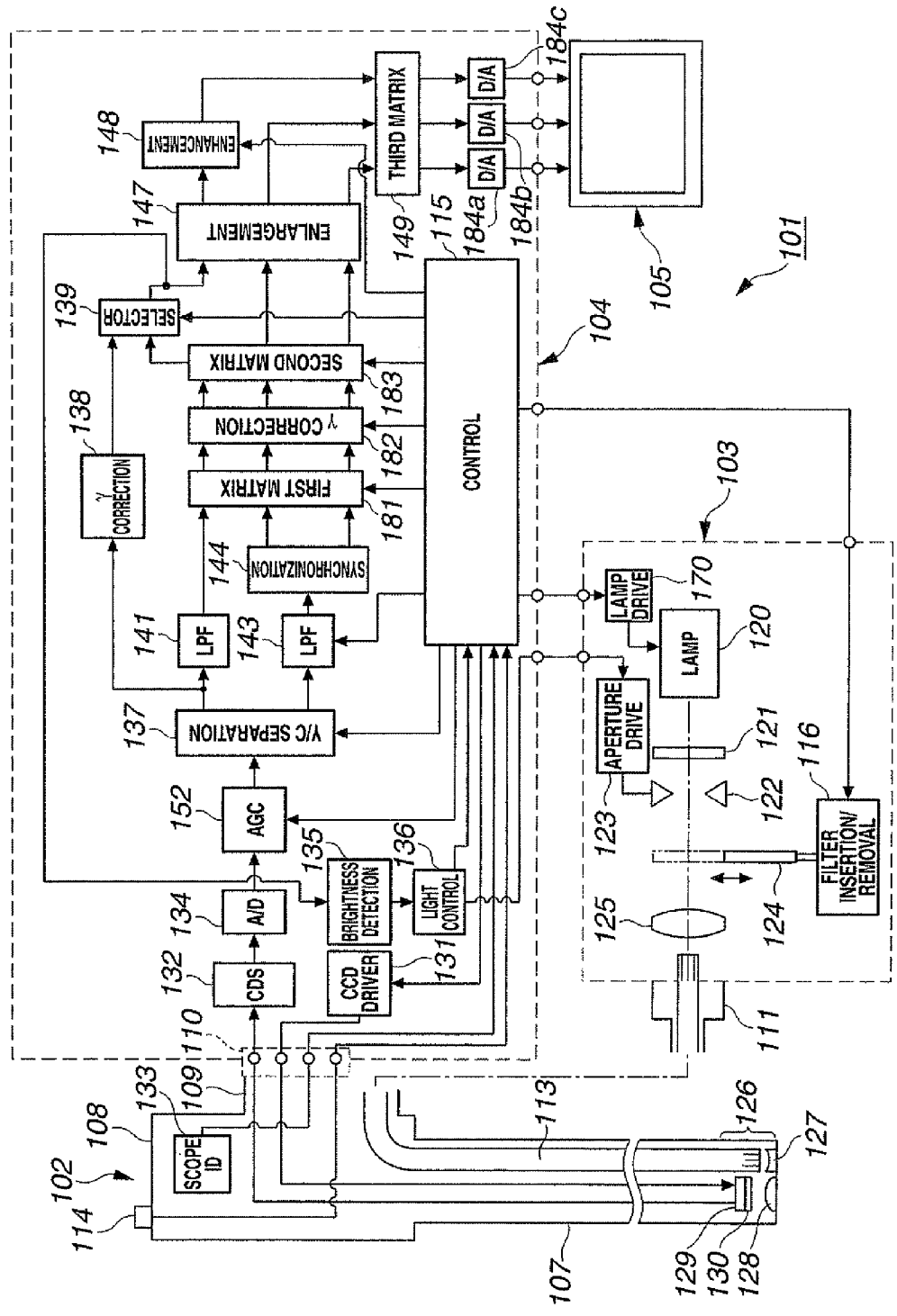
FIG. 10 is a diagram showing one example of a configuration of main parts in the endoscopic device of a modified example of the present embodiment.
Figure 11:
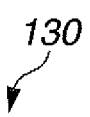
FIG. 11 is a diagram showing one example of a configuration of a color separation filter arranged in the endoscope in the endoscopic device of the modified example of the present embodiment.
Figure 12:
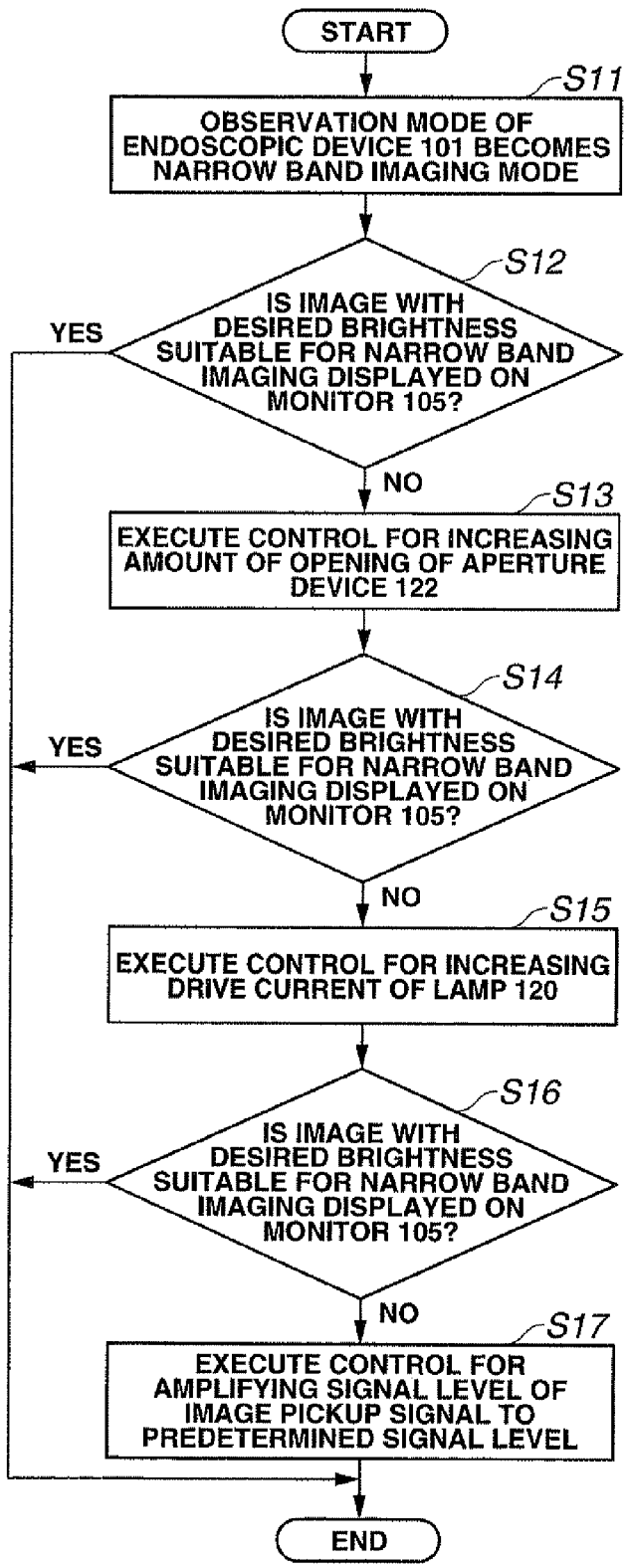
FIG. 12 is a diagram showing one example of a process executed when the endoscopic device of the modified example of the present embodiment is in the narrow band imaging mode.

Embodiments of the present invention will now be described with reference to the drawings. FIG. 1 is a diagram showing one example of a configuration of main parts in an endoscopic device of the present embodiment. FIG. 2 is a diagram showing one example of a configuration of a rotating filter arranged on a light source device in the endoscopic device of the present embodiment. FIG. 3 is a diagram showing spectral characteristics of a filter used by the light source device for directing illumination light for normal observation in the endoscopic device of the present embodiment. FIG. 4 is a diagram showing spectral characteristics of a filter used by the light source device for directing illumination light for narrow band imaging in the endoscopic device of the present embodiment. FIG. 5 is a diagram showing a state of a drive current supplied to a lamp when the endoscopic device of the present embodiment is in a normal observation mode. FIG. 6 is a diagram showing a state of a drive current supplied to the lamp in a first drive current control performed when the endoscopic device of the present embodiment is in a narrow band imaging mode. FIG. 7 is a diagram showing a state of a drive current supplied to the lamp in a second drive current control performed when the endoscopic device of the present embodiment is in the narrow band imaging mode. FIG. 8 is a diagram showing a state of a drive current supplied to the lamp in a third drive current control performed when the endoscopic device of the present embodiment is in the narrow band imaging mode. FIG. 9 is a diagram showing one example of a process executed when the endoscopic device of the present embodiment is in the narrow band imaging mode. FIG. 10 is a diagram showing one example of a configuration of main parts in the endoscopic device of a modified example of the present embodiment. FIG. 11 is a diagram showing one example of a configuration of a color separation filter arranged in the endoscope in the endoscopic device of the modified example of the present embodiment. FIG. 12 is a diagram showing one example of a process executed when the endoscopic device of the modified example of the present embodiment is in the narrow band imaging mode.

As shown in FIG. 1, the main parts of the endoscopic device 1 comprises: an endoscope 2 inserted into a body cavity, the endoscope 2 picking up an image of a subject such as biological tissues in the body cavity and outputting the image as an image pickup signal; a light source device 3 that emits illumination light to the endoscope 2 for illuminating the subject; a video processor 4 that drives image pickup unit embedded in the endoscope 2, applies a signal process to the image pickup signal outputted from the endoscope 2, and outputs the signal as a video signal; and a monitor 5 as display unit for displaying the image of the subject based on the video signal outputted from the video processor 4.

The endoscope 2 comprises an elongated insertion portion 7 inserted into a body cavity and an operation portion 8 arranged at the proximal end of the insertion portion 7. The insertion portion 7 comprises a distal end portion 22 at the distal end side.

The endoscope 2 also comprises a mode changing switch 20 with which observation mode switching of a normal observation mode, a narrow band imaging mode, and the like is instructed with an operation of an operator or the like. The instruction of the observation mode switching performed by the mode changing switch 20 is outputted to the video processor 4 as a mode switching instruction signal. The mode changing switch 20 is not limited to be arranged on the endoscope 2, but may be arranged, for example, on the front panel not shown of the video processor 4 or may be configured as a predetermined key of a keyboard not shown connectable to the video processor 4.

The endoscope 2 further comprises a scope ID generating circuit 28 that outputs, for example, specific identification information (abbreviated as scope ID), such as model information, which is information used for setting parameters or the like in various signal processes executed by the video processor 4.

The distal end portion 22 of the endoscope 2 comprises: an illumination lens 23 attached to an illumination window not shown; an objective lens 24 arranged adjacent to the illumination window and attached to an observation window not shown; and a CCD (charge coupled device) 25 that is an image pickup device arranged at the imaging position of the objective lens 24. The CCD 25 as image pickup unit picks up an image of the subject image-formed by the objective lens 24 and outputs the picked up image of the subject as an image pickup signal. The image pickup signal outputted from the CCD 25 is outputted to the video processor 4 through a signal line 26. The signal line 26 is removably connectable to the video processor 4 through a connector not shown.

A light guide 9 for transmitting the illumination light emitted from the light source device 3 is inserted inside the insertion portion 7. One end of the light guide 9 having the light outgoing surface is arranged on the light incoming side of the illumination lens 23, while the other end of the light guide 9 having the light incoming surface is removably connectable to the light source device 3.

The light source device 3 comprises a lamp drive circuit 10; a lamp 11; a heat wave cut-off filter 12 that cuts off the heat wave of the light emitted by the lamp 11; an aperture device 13 that controls the amount of light emitted through the heat wave cut-off filter 12; a rotating filter 14 that is arranged on the optical path of the lamp 11 and that converts the light emitted from the aperture device 13 as aperture unit to frame sequential light to thereby allow the light to be emitted; a condenser lens 15 that condenses the light emitted from the rotating filter 14 and that emits the light to the light incoming surface of the light guide 9; a rotating filter motor 17 that rotates and drives the rotating filter 14; a move motor 18 that serves as a driving source for moving the rotating filter 14; and a control circuit 16 that controls the rotation of the rotating filter motor 17.

The lamp drive circuit 10 supplies a drive current to the lamp 11 based on a brightness control signal outputted from a light control circuit 33 described below.

The lamp 11 as light source unit comprises, for example, a xenon lamp and the like and emits white light at least including a visible region band based on the drive current supplied from the lamp drive circuit 10.

As shown in FIG. 2, the rotating filter 14 is a disc-shaped filter having a rotating shaft at the center and comprises a first filter group 14A arranged at an outer circumferential direction part and a second filter group 14B arranged at an inner circumferential direction part.

The first filter group 14A comprises an R1 filter 14r1 that mainly penetrates light in the red band, a G1 filter 14g1 that mainly penetrates light in the green band, and a B1 filter 14b1 that mainly penetrates light in the blue band, the filters of which are set to have spectral characteristics as shown in FIG. 3.

The second filter group 14B comprises an R2 filter 14r2 that penetrates light in a band narrower than the R1 filter 14r1, a G2 filter 14g2 that penetrates light in a band narrower than the G1 filter 14g1, and a B2 filter 14b2 that only penetrates light in a band narrower than the B1 filter 14b1, the filters of which are set to have discrete spectral characteristics as shown in FIG. 4. With such a configuration, when arranged on the optical path of the lamp 11, the second filter group 14B functions as spectral unit for penetrating light in the band based on the spectral characteristics among the lights emitted from the lamp 11.

The rotating filter 14 rotates with the rotation and drive of the rotating filter motor 17 controlled by the control circuit 16. With such a configuration, the rotating filter 14 rotates at a rotational speed of, for example, 20 rotations per second.

The rotating filter 14 is further designed to move along with the rotating filter motor 17 in a direction indicated by an arrow A of FIG. 1, or in the direction perpendicular to the optical path of the lamp 11, with the action of the move motor 18.

The move motor 18 comprises a pinion gear 18a arranged on the rotating shaft of the move motor 18. The pinion gear 18a engages with a rack 17a integrally arranged with the rotating filter motor 17 and constitutes a rack and pinion mechanism.

The move motor 18 is driven by the action of a mode switching circuit 21 and moves the rotating filter 14 and the rotating filter motor 17 in the direction indicated by the arrow A of FIG. 1 through the rack and pinion mechanism. Specifically, the move motor 18 rotates in the normal direction or in the opposite direction to move the rotating filter 14 and the rotating filter motor 17 so that one filter in the first filter group 14A or the second filter group 14B corresponding to the observation mode is arranged on the optical path of the lamp 11.

For example, when the mode changing switch 20 is operated by an operator or the like and a mode switching instruction signal is outputted to the video processor 4, the mode switching circuit 21 arranged on the video processor 4 outputs an observation mode switching signal, which will be described later, to the move motor 18. The move motor 18 rotates in the normal direction or in the opposite direction based on the observation mode switching signal, thereby enabling to mount one filter in the first filter group 14A or the second filter group 14B corresponding to the observation mode on the optical path of the lamp 11.

The mode switching circuit 21 as mode switching unit outputs an observation mode switching signal for informing the move motor 18 of the light source device 3, an automatic gain control circuit (hereinafter abbreviated as AGC circuit) 35, a noise suppression circuit 36, a color conversion circuit 38, a switching circuit 40, and a light control parameter switching circuit 50 that the observation mode is switched from one observation mode to another observation mode, based on the mode switching instruction signal outputted from the mode changing switch 20. The configurations of the AGC circuit 35, the noise suppression circuit 36, the color conversion circuit 38, the switching circuit 40, and the light control parameter switching circuit 50 will be described in detail later.

When the first filter group 14A is arranged on the optical path of the lamp 11, illumination light for normal observation, which serves as the illumination light used in the normal observation mode and which has a band substantially the same as that of the white light emitted from the lamp 11, enters the light incoming surface of the light guide 9 through the condenser lens 15. Meanwhile, when the second filter group 14B is arranged on the optical path of the lamp 11, illumination light for narrow band imaging, which serves as illumination light used in the narrow band imaging mode and which has a narrower band than the illumination light for normal observation, enters the light incoming surface of the light guide 9 through the condenser lens 15.

After entering the light incoming surface of the light guide 9, the illumination light for normal observation and the illumination light for narrow band imaging are emitted to a subject, such as biological tissues, through the illumination lens 23 arranged on the light outgoing surface side.

After the objective lens 24 has formed an image of the subject illuminated by the illumination light emitted from the illumination lens 23, the CCD 25 picks up the image. The image of the subject picked up by the CCD 25 is outputted as an image pickup signal to the video processor 4 through the signal line 26.

The CCD 25 is connected to a CCD driver 29, which outputs a CCD drive signal to the CCD 25, and to a preamp 30 that are arranged on the video processor 4. With such a configuration, the CCD 25 is driven based on the CCD drive signal outputted from the CCD driver 29. The CCD 25 generates an image pickup signal in the driving state and outputs the generated image pickup signal to the preamp 30.

The image pickup signal outputted from the CCD 25 to the video processor 4 is amplified by the preamp 30, and a process circuit 31 performs correlated double sampling, noise removal, or the like. An A/D conversion circuit 32 converts the image pickup signal to a digital signal, which is then inputted to a white balance circuit 34.

The white balance circuit 34 executes a white balance process to the inputted imaged pickup signal and then outputs the processed image pickup signal to the AGC circuit 35.

Based on the observation mode switching signal outputted from the mode switching circuit 21 and the brightness control signal outputted from the light control circuit 33, the AGC circuit 35 as image pickup signal amplification unit amplifies the image pickup signal outputted from the white balance circuit 34 to a predetermined signal level in accordance with the observation mode when the brightness control signal is inputted. The AGC circuit 35 then outputs the amplified image pickup signal to the noise suppression circuit 36 and the switching circuit 40.

Based on the observation mode switching signal outputted from the mode switching circuit 21, the switching circuit 40 connects a contact a and disconnects a contact b in the normal observation mode and connects the contact b and disconnects the contact a in the narrow band imaging mode.

Based on the timing signal outputted from the timing generator 49 and the observation mode switching signal outputted from the mode switching circuit 21, the noise suppression circuit 36 executes a noise suppression process to image pickup signals (hereinafter, referred to as R2 signal, G2 signal, and B2 signal) of the images of the subject picked up by the CCD 25 under the light penetrated through the R2 filter 14r2, the G2 filter 14g2, and the B2 filter 14b2, while switching the parameters to adapt the parameters to the image pickup signals. The noise suppression circuit 36 then outputs the image pickup signal, to which the noise suppression process is executed, to a synchronization circuit 37. The noise suppression circuit 36 may be configured to execute the noise suppression process while changing or switching the parameters based on the scope ID outputted from the scope ID generating circuit 28.

The R2 signal, the G2 signal, and the B2 signal, which are image pickup signals outputted from the noise suppression circuit 36, are synchronized and outputted by the synchronization circuit 37 and then inputted to the color conversion circuit 38.

The color conversion circuit 38 uses, for example, a 3 by 3 matrix to execute a color conversion process to the R2 signal, the G2 signal, and the B2 signal, which are image pickup signals synchronized and outputted by the synchronization circuit 37, and then outputs the R2 signal, the G2 signal, and the B2 signal, to which the color conversion process is executed, to a frame sequential circuit 39.

The frame sequential circuit 39 comprises a frame memory not shown that stores the R2 signal, the G2 signal, and the B2 signal and sequentially reads out the stored R2 signal, the G2 signal, and the B2 signal as color component image signals to thereby convert the signals to frame sequential R2, G2, and B2 image data. The frame sequential circuit 39 then outputs the frame sequential R2, G2, and B2 image data to the switching circuit 40.

A γ correction circuit 41 applies a γ-correction to the image pickup signal outputted from the switching circuit 40 when the contact a is conducted or to the image data outputted when the contact b is conducted. The image pickup signal or the image data are enlarged and interpolated by an enlargement circuit 42 and then inputted to an enhancement circuit 43.

If the contact a is conducted in the switching circuit 40, the image pickup signal outputted from the AGC circuit 35 is inputted not only to the γ correction circuit 41, but also to the light control circuit 33.

If the contact b is conducted in the switching circuit 40, the frame sequential R2, G2, and B2 image data is inputted not only to the γ correction circuit 41, but also to the light control circuit 33.

The enhancement circuit 43 applies a process of structure enhancement or edge enhancement to the video signal or the image data outputted from the enlargement circuit 42 and then outputs the processed image pickup signal or the image data to a selector 44.

The image pickup signal or the image data outputted from the enhancement circuit 43 is inputted to a synchronization circuit 45 through the selector 44.

The synchronization circuit 45 comprises three memories 45a, 45b, and 45c. The synchronization circuit 45 stores and synchronizes R (red), G (green), and B (blue) components included in the image pickup signal or R2, R2, and B2 components included in the image data and then outputs the synchronized image pickup signal or the image data to an image processing circuit 46.

The image pickup signal or the image data synchronized and outputted by the synchronization circuit 45 is applied with image processing, such as a color blur correction of moving images, by the image processing circuit 46 and then inputted to D/A conversion circuits 47a, 47b, and 47c.

The D/A conversion circuits 47a, 47b, and 47c store R, G, and B components included in the image pickup signal or the R2, G2, and B2 components included in the image data, convert the stored components to analog video signals, and then outputs the video signals to the monitor 5.

The light control parameter switching circuit 50 detects the observation mode of the endoscopic device 1 based on the observation mode switching signal outputted from the mode switching circuit 21 and outputs light control parameters based on the detection result to the light control circuit 33.

The light control circuit 33 as brightness control unit applies a predetermined control and process to the aperture device 13, the lamp drive circuit 10, and the AGC circuit 35 for amplifying and adjusting the brightness of an image when the image of the subject picked up by the endoscope 2 is displayed on the monitor 5 as an image, based on the image pickup signal inputted when the contact a of the switching circuit 40 is conducted or the R2, G2, and B2 image data inputted when the contact b of the switching circuit 40 is conducted and the light control parameters outputted from the light control parameter switching circuit 50. The predetermined control and process executed by the light control circuit 33 will be illustrated in detail later.

An action of the endoscopic device 1 of the present embodiment will now be described.

An operator or the like first brings the endoscopic device 1 into the initial state as shown in FIG. 1 by connecting the endoscope 2 to the light source device 3 and the video processor 4 and by applying power to the above components and the monitor 5. The endoscopic device 1 is set to the normal observation mode in the initial state.

In the normal observation mode, the mode switching circuit 21 outputs the observation mode switching signal to the move motor 18 to arrange the first filter group 14A on the optical path of the lamp 11. With the first filter group 14A being arranged on the optical path of the lamp 11, the light source device 3 emits the illumination light for normal observation. The illumination light for normal observation emitted from the light source device 3 is transmitted by the light guide 9 and then emitted to the subject through the illumination lens 23.

The CCD 25 picks up an image of the subject illuminated by the illumination light for normal observation and image-formed by the objective lens 24 and then outputs the picked up image of the subject to the video processor 4 as an image pickup signal.

The video processor 4 applies the processes in the above components to the image pickup signal outputted from the CCD 25 to generate a video signal and outputs the video signal to the monitor 5. In this way, the image of the subject in the normal observation is displayed on the monitor 5. More specifically, in the normal observation mode, after the processes such as amplification by the preamp 30 or the like, the image pickup signal outputted from the AGC circuit 35 is inputted to the γ correction circuit 41 through the switch 40, without being subjected to the processes in the noise suppression circuit 36, the synchronization circuit 37, the color conversion circuit 38, and the frame sequential circuit 39. After execution of the processes such as the γ correction process, the enhancement process, and the structure enhancement process, the image pickup signal is inputted to the synchronization circuit 45 through the selector 44 and then synchronized. The image pickup signal is further subjected to a moving image color blur correction or the like, converted to an analog video signal, and then outputted to the monitor 5.

With the image of the subject in the normal observation being displayed on the monitor 5, based on the image pickup signal inputted when the contact a of the switching circuit 40 is conducted, the light control circuit 33 outputs a brightness control signal to the aperture device 13 to thereby control the aperture device 13 for opening the aperture when detecting that the image is not displayed as an image with a desired brightness suitable for the normal observation. The aperture device 13 then opens the aperture based on the brightness control signal outputted from the light control circuit 33.

Subsequently, based on the image pickup signal inputted when the contact a of the switching circuit 40 is conducted, the light control circuit 33 further outputs a brightness control signal to the AGC circuit 35 to thereby control the AGC circuit 35 for amplifying the signal level of the image pickup signal to a predetermined signal level when detecting that the image of the subject displayed on the monitor 5 is not displayed as an image with a desired brightness suitable for the normal observation even when the aperture device 13 has fully opened the aperture.

With such a control by the light control circuit 33, an image of the subject having a desired brightness suitable for the normal observation is displayed on the monitor 5.

As shown in FIG. 5, in the normal observation, the light control circuit 33 controls the lamp drive circuit 10 to maintain the drive current of the lamp 11 to, for example, 18 amperes as a first drive current.

Subsequently, once the operator or the like operates the mode changing switch 20 to output a switching instruction signal to the processor 4 for switching the observation mode of the endoscopic device 1 from the normal observation mode to the narrow band imaging mode, the mode switching circuit 21 outputs the observation mode switching signal to the move motor 18, the switching circuit 40, and the light control parameter switching circuit 50.

The mode switching circuit 21 outputs the observation mode switching signal to the move motor 18 to arrange the second filter group 14B on the optical path of the lamp 11. The mode switching circuit 21 outputs the observation mode switching signal to the switching circuit 40 to disconnect the contact a and connect the contact b. The mode switching circuit 21 further outputs the observation mode switching signal to the light control parameter switching circuit 50 to switch the light control parameters outputted to the light control circuit 33. With execution of the control, the observation mode of the endoscopic device 1 is switched from the normal observation mode to the narrow band imaging mode (step S1 of FIG. 9).

With the second filter group 14B being arranged on the optical path of the lamp 11, the light source device 3 emits the illumination light for narrow band imaging. The illumination light for narrow band imaging emitted from the light source device 3 is transmitted by the light guide 9 and then emitted to the subject through the illumination lens 23.

Immediately after the observation mode of the endoscopic device 1 is switched to the narrow band imaging mode, the light control circuit 33 outputs the brightness control signal to the lamp drive circuit 10 to execute the first drive current control, which will be described later, to the lamp drive circuit 10 so that the duty ratio of the drive currents supplied from the lamp drive circuit 10 to the lamp 11 is set to a state as shown for example in FIG. 6, based on the light control parameters outputted from the light control parameter switching circuit 50 (step S2 of FIG. 9).

Based on the brightness control signal outputted from the light control circuit 33, the lamp drive circuit 10 sets the duty ratio of the first drive current and the second drive current in which the drive current is set higher than that of the first drive current, such as 20 amperes, in accordance with the rotational speed of the rotating filter 14 as shown in FIG. 6 and supplies the drive currents to the lamp 11.

Specifically, for example, the light penetrated through the R2 filter 14r2, the light penetrated through the G2 filter 14g2, and the light penetrated through the R2 filter 14b2 are emitted to the subject for 1/60 second each while the rotating filter 14 rotates once, if the rotational speed of the rotating filter 14 is 20 rotations per second. If, for example, a period of 1/60 second in which the light penetrated through the R2 filter 14r2 is directed to the subject is defined as a first cycle, the lamp drive circuit 10 supplies a first drive current to the lamp 11 for Ra second and supplies a second drive current for Rb second during the first cycle, as shown in FIG. 6. If, for example, a period of 1/60 second in which the light penetrated through the G2 filter 14g2 is directed to the subject is defined as a second cycle, the lamp drive circuit 10 supplies a first drive current to the lamp 11 for Ga second and supplies a second drive current for Gb second during the second cycle, as shown in FIG. 6. If, for example, a period of 1/60 second in which the light penetrated through the B2 filter 14b2 is directed to the subject is defined as a third cycle, the lamp drive circuit 10 supplies a first drive current to the lamp 11 for Ba second and supplies a second drive current for Bb second during the third cycle, as shown in FIG. 6.

Meanwhile, the CCD 25 picks up the image of the subject illuminated by the illumination light for narrow band imaging and image-formed by the objective lens 24 and outputs the picked up image of the subject to the video processor 4 as an image pickup signal.

The video processor 4 applies the processes in the above components to the image pickup signal outputted from the CCD 25 to generate a video signal and outputs the video signal to the monitor 5. In this way, the image of the subject in the narrow band imaging is displayed on the monitor 5. More specifically, in the narrow band imaging mode, after execution of the processes such as amplification by the preamp 30 or the like, the image pickup signal outputted from the AGC circuit 35 is applied with the noise suppression process by the noise suppression circuit 36, synchronized by the synchronization circuit 37, and the color conversion process is applied by the color conversion circuit 38. The image pickup signal is then converted to image data in the frame sequential circuit 39 and inputted to the γ correction circuit 41 through the switching circuit 40. The image data inputted to the γ correction circuit 41 is thereafter applied with similar processes as the processes applied to the image pickup signal in the normal observation mode and then outputted to the monitor 5 as a video signal.

With the image of the subject in the narrow band imaging being displayed on the monitor 5, based on the image data inputted when the contact b of the switching circuit 40 is conducted, when the light control circuit 33 detects that the image is not displayed as an image with a desired brightness suitable for the narrow band imaging (step S3 of FIG. 9), the light control circuit 33 outputs a brightness control signal to the aperture device 13 to thereby control the aperture device 13 for opening the aperture (step S4 of FIG. 9). The aperture device 13 then opens the aperture based on the brightness control signal outputted from the light control circuit 33.

Subsequently, based on the image data inputted when the contact b of the switching circuit 40 is conducted, when the light control circuit 33 detects that the image of the subject displayed on the monitor 5 is not displayed as an image with a desired brightness suitable for the narrow band imaging even when the aperture device 13 has fully opened the aperture (step S5 of FIG. 9), the light control circuit 33 outputs a brightness control signal to the lamp drive circuit 10. By outputting the brightness control signal to the lamp drive circuit 10, the light control circuit 33 executes, as will be described below, a second drive current control to the lamp drive circuit 10 so that the duty ratio of the drive currents supplied from the lamp drive circuit 10 to the lamp 11 is set to a state as shown in FIG. 7 (step S6 of FIG. 9).

Based on the brightness control signal outputted from the light control circuit 33, the lamp drive circuit 10 sets the duty ratio of the first drive current and the second drive current in accordance with the rotational speed of the rotating filter 14 as shown in FIG. 7 and supplies the drive currents to the lamp 11.

Specifically, for example, the lamp drive circuit 10 supplies the first drive current for Rc second, which is a time shorter than Ra second, and the second drive current for Rd second, which is a time longer than Rb second, to the lamp 11, during the first cycle that is a period in which the light penetrated through the R2 filter 14*r*2 is directed to the subject, as shown in FIG. 7. The lamp drive circuit 10, for example, supplies the first drive current for Gc second, which is a time shorter than Ga second, and the second drive current for Gd second, which is a time longer than Gb second, to the lamp 11, during the second cycle that is a period in which the light penetrated through the G2 filter 14*g*2 is directed to the subject, as shown in FIG. 7. The lamp drive circuit 10, for example, further supplies the second drive current to the lamp 11 during the third cycle (Bc second shown in FIG. 7) that is a period in which the light penetrated through the B2 filter 14*b*2 is directed to the subject, as shown in FIG. 7.

Thus, the light control circuit 33 applies the second drive current control, in which the supply period of the second drive current to the lamp 11 is extended compared to the first drive current control, to the lamp drive circuit 10.

Furthermore, based on the image data inputted when the contact b of the switching circuit 40 is conducted, when the light control circuit 33 detects that the image of the subject displayed on the monitor 5 is not displayed as an image with a desired brightness suitable for the narrow band imaging even after the aperture device 13 has fully opened the aperture and the second drive current control is executed (step S7 of FIG. 9), the light control circuit 33 outputs a brightness control signal to the lamp drive circuit 10. By outputting the brightness control signal to the lamp drive circuit 10, the light control circuit 33 executes, as will be described below, a third drive current control to the lamp drive circuit 10 so that the duty ratio of the drive currents supplied from the lamp drive circuit 10 to the lamp 11 is set to a state as shown in FIG. 8 (step S8 of FIG. 9).

Based on the brightness control signal outputted from the light control circuit 33, the lamp drive circuit 10 sets the duty ratio of the first drive current, the second drive current, and a third drive current set at, for example, 22 amperes as a drive current higher than the second drive current in accordance with the rotational speed of the rotating filter 14 as shown in FIG. 8 and supplies the drive currents to the lamp 11.

Specifically, for example, the lamp drive circuit 10 supplies the first drive current for Re second, which is a time shorter than Rc second, and the second drive current for Rf second, which is a time longer than Rd second, to the lamp 11, during the first cycle that is a period in which the light penetrated through the R2 filter 14*r*2 is directed to the subject as shown in FIG. 8. The lamp drive circuit 10, for example, supplies the first drive current for Ge second, which is a time shorter than Gc second and the second drive current for Gf second, which is a time longer than Gd second, to the lamp 11, during the second cycle that is a period in which the light penetrated through the G2 filter 14*g*2 is directed to the subject, as shown in FIG. 8. The lamp drive circuit 10, for example, further supplies the third drive current for Bd second and the second drive current for Be second to the lamp 11 during the third cycle in which the light penetrated through the B2 filter 14*b*2 is directed to the subject, as shown in FIG. 8.

Thus, the light control circuit 33 applies the third drive current control to the lamp drive circuit 10, the control in which the supply period of the second drive current to the lamp 11 is extended compared to the second drive current control, and in which a supply period of the third drive current is provided in addition to the supply period of the first drive current and the supply period of the second drive current.

Based on the image pickup signal inputted when the contact b of the switching circuit 40 is conducted, when the light control circuit 33 detects that the image of the subject displayed on the monitor 5 is not displayed as an image with a desired brightness suitable for the narrow band imaging even after the aperture device 13 has fully opened the aperture and the second drive current control as well as the third drive current control are executed (step S9 of FIG. 9), the light control circuit 33 outputs a brightness control signal to the AGC circuit 35 to thereby apply a control to the AGC circuit 36 for amplifying the signal level of the image pickup signal to a predetermined signal level (step S10 of FIG. 9).

The series of controls described above, i.e., the control to the aperture device 13 for opening the aperture, the control to the lamp drive circuit 10 for changing the drive current to be supplied to the lamp 11 in stages, and the control to the AGC circuit 35 for amplifying the signal level of the image pickup signal, are executed in the above order in the endoscopic device 1 in the narrow band imaging mode to thereby display an image with as little reduction of S/N as possible and a desired brightness suitable for observation on the monitor 5.

In the present embodiment, to obtain the advantages described above, an endoscopic device 101 may be used instead of the endoscopic device 1, as will be described below.

As shown in FIG. 10, the main parts of the endoscopic device 101 comprises: an endoscope 102 inserted into a body cavity, the endoscope 102 picking up an image of a subject such as biological tissues in the body cavity and outputting the image as an image pickup signal; a light source device 103 that emits illumination light to the endoscope 102 for illuminating the subject; a video processor 104 that drives image pickup unit embedded in the endoscope 102, applies a signal process to the image pickup signal outputted from the endoscope 102, and outputs the signal as a video signal; and a monitor 105 that displays the image of the subject based on the video signal outputted from the video processor 104.

The endoscope 102 comprises an elongated insertion portion 107 inserted into a body cavity, an operation portion 108 arranged at the proximal end of the insertion portion 107, and a universal cable 109 extending from part of the operation portion 108. The insertion portion 107 comprises a distal end portion 126 on the distal end side. A signal connector 110 removably disposed on the video processor 104 and a light guide connector 111 removably disposed on the light source device 103 are arranged at the end portion of the universal cable 109.

The endoscope 102 comprises a mode changing switch 114 with which observation mode switching of a normal observation mode, a narrow band imaging mode, and the like is instructed by an operation by an operator or the like. The instruction of the observation mode switching provided by the mode changing switch 114 is outputted to the video processor 104 as a mode switching instruction signal. The mode changing switch 114 is not limited to be arranged on the endoscope 102, but may be arranged on the front panel not shown of the video processor 104 or may be configured as a predetermined key of a keyboard not shown connectable to the video processor 104.

The endoscope 102 further comprises a scope ID generating circuit 133 that outputs specific identification information (abbreviated as scope ID), such as model information, which is information used for setting parameters or the like in various signal processes executed by the video processor 104.

The distal end portion 126 of the endoscope 102 comprises: an illumination lens 127 attached to an illumination window not shown; an objective lens 128 arranged adjacent to the illumination window and attached to an observation window not shown; and a CCD (charge coupled device) 129 that is an image pickup device arranged at the image-forming position of the objective lens 128. The CCD 129 picks up an image of the subject image-formed by the objective lens 128 and outputs the picked up image of the subject to the video processor 104 as an image pickup signal. A complementary filter, such as the one shown in FIG. 11, as a color separation filter 130 for performing an optical color separation pixel by pixel is arranged on the image-pickup plane of the CCD 129.

The color separation filter 130 comprises four color chips of magenta (Mg), green (G), cyan (Cy), and yellow (Ye) in front of each pixel. More specifically, Mg color chips and G color chips are alternately arranged in the horizontal direction of the color separation filter 130, and the color chips are arranged in the orders of Mg, Cy, Mg, Ye, and G, Ye, C, Cy in the vertical direction.

A light guide 113 for transmitting the illumination light emitted from the light source device 103 is inserted inside the insertion portion 107 and the universal cable 109. One end of the light guide 113 having the light outgoing surface is arranged on the light incoming side of the illumination lens 127, while the other end having the light incoming surface is arranged inside the light guide connector 111.

The light source device 103 comprises a filter insertion/removal mechanism 116, a lamp 120, a heat wave cut-off filter 121 that cuts off the heat wave of the light emitted by the lamp 120, an aperture device 122 that controls the amount of light emitted through the heat wave cut-off filter 121, an aperture drive circuit 123, a narrow band imaging filter 124 as spectral unit having spectral characteristics substantially the same as the spectral characteristics shown in FIG. 4, a condenser lens 125, and a lamp drive circuit 170.

Based on an observation mode switching signal outputted from the control circuit 115 described below, the filter insertion/removal mechanism 116 removes the narrow band imaging filter 124 from the optical path of the lamp 120 in the normal observation mode and arranges the narrow band imaging filter 124 on the optical path of the lamp 120 in the narrow band imaging mode.

The lamp 120 as light source unit comprises, for example, a xenon lamp, which emits white light, and emits white light at least including a visible region band based on the drive current supplied from the lamp drive circuit 170.

Based on a brightness control signal outputted from the light control circuit 136 described below, the aperture drive circuit 123 adjusts the amount of opening of the aperture device 122 as aperture unit.

The condenser lens 125 condenses normal observation illumination light emitted as illumination light having a band substantially similar to the white light without passing through the narrow band imaging filter 124 and narrow band imaging illumination light emitted as illumination light having a band shown in FIG. 4 by passing through the narrow band imaging filter 124 arranged on the optical path of the lamp 120. The condenser lens 125 then emits the light to the light incoming surface of the light guide 113 arranged on the light guide connector 111.

The lamp drive circuit 170 supplies a drive current to the lamp 120 based on a brightness control signal outputted from the control circuit 115 described below.

For example, when the mode changing switch 114 is operated by an operator or the like and a mode switching instruction signal is outputted to the video processor 104, the control circuit 115 arranged on the video processor 104 outputs an observation mode switching signal, which will be described later, to the filter insertion/removal mechanisms 116. Based on the observation mode switching signal, the filter insertion/removal mechanism 116 then moves the narrow band imaging filter 124 so as to remove the narrow band imaging filter 124 from the optical path of the lamp 120 or to arrange the narrow band imaging filter 124 on the optical path of the lamp 120.

Based on the mode switching instruction signal outputted from the mode changing switch 114, the control circuit 115 as mode switching unit outputs an observation mode switching signal for informing the filter insertion/removal mechanism 116 of the light source device 103, a CCD driver 131, a Y/C separation circuit 137, a selector 139, a low-pass filter (described as LPF in FIG. 10) 143, an enhancement circuit 148, a first matrix circuit 181, a γ correction circuit 182, and a second matrix circuit 183 that the observation mode has switched from one observation mode to another observation mode. As the control circuit 115 outputs the observation mode switching signal to the above components, the endoscopic device 101 switches from one observation mode to another observation mode. Configurations of the Y/C separation circuit 137, the selector 139, the low-pass filter 143, the enhancement circuit 148, the first matrix circuit 181, the γ correction circuit 182, and the second matrix circuit 183 will be described later.

The control circuit 115 that constitutes part of the brightness control unit in the endoscopic device 101 outputs a brightness control signal to an AGC circuit 152 and a lamp drive circuit 170 described below, based on a control switching signal outputted from the light control circuit 136, which will be described later.

When the narrow band imaging filter 124 is removed from the optical path of the lamp 120, the illumination light for normal observation, which has a band substantially the same as the white light emitted from the lamp 11, as illumination light used in the normal observation mode enters the light incoming surface of the light guide 113 through the condenser lens 125. On the other hand, when the narrow band imaging filter 124 is arranged on the optical path of the lamp 120, the illumination light for narrow band imaging, which has a narrower band than the illumination light for normal observation, as illumination light used in the narrow band imaging mode enters the light incoming surface of the light guide 113 through the condenser lens 125.

After entering the light incoming surface of the light guide 113, the illumination light for normal observation and the illumination light for narrow band imaging are emitted to a subject such as biological tissues through the illumination lens 127 arranged on the light outgoing surface side.

The subject illuminated by the illumination light emitted from the illumination lens 127 is image-formed by the objective lens 128 and then picked up by the CCD 129. The image of the subject picked up by the CCD 129 as image pickup unit is outputted to the video processor 104 as an image pickup signal through a signal line whose one end is connected to the CCD 129 and the other end is connected to the signal connector 110.

The CCD 129 is connected to the CCD driver 131, which outputs a CCD drive signal to the CCD 129, and a correlated double sampling circuit (hereinafter abbreviated CDS circuit) 132 arranged in the video processor 104. Having such a configuration, the CCD 129 is driven based on the CCD drive signal outputted from the CCD driver 131, generates an image pickup signal in the driving state, and outputs the generated image pickup signal to the CDS circuit 132. The CCD driver 131 outputs the CCD drive signal to the CCD 129 based on the observation mode switching signal outputted from the control circuit 115 so that the CCD 129 is brought into a driving state in accordance with the observation mode.

The image pickup signal outputted from the CCD 129 to the video processor 104 is subjected to the correlated double sampling or the like by the CDS circuit 132, converted to a digital signal by an A/D conversion circuit 134, and inputted to the AGC circuit 152.

Based on the brightness control signal outputted from the control circuit 115, the AGC circuit 152 as image pickup signal amplification unit amplifies the image pickup signal outputted from the A/D conversion circuit 134 to a predetermined signal level in accordance with the observation mode and outputs the amplified image pickup signal to the Y/C separation circuit 137, when the brightness control signal is inputted.

The Y/C separation circuit 137 generates a luminance signal and a color difference signal based on the image pickup signal outputted from the AGC circuit 152, outputs the luminance signal to a γ correction circuit 138 and a low-pass filter (described as LPF in FIG. 10) 141, and outputs the color difference signal to the low-pass filter 143.

The luminance signal outputted from the Y/C separation circuit 137 to the γ correction circuit 138 is subjected to a γ correction by the γ correction circuit 138 and then inputted to a brightness detection circuit 135 through the selector 139.

The brightness detection circuit 135 calculates, for example, an average luminance of the luminance signals based on the luminance signals outputted from the selector 139 to thereby detect the brightness of the luminance signals, and then outputs information related to the detected brightness to the light control circuit 136 as a brightness signal.

Based on the brightness signal outputted from the brightness detection circuit 135, the light control circuit 136 constituting part of the brightness control unit in the endoscopic device 101 outputs a brightness control signal to the aperture drive circuit 123 for changing the amount of opening of the aperture device 122. When detecting that the aperture device 122 is fully opened, the light control circuit 136 outputs a control switching signal to the control circuit 115.

After the high frequency components in accordance with the pass band included in a low-pass filter 141 are cut, the luminance signal outputted from the Y/C separation circuit 137 to the low-pass filter 141 are inputted to the first matrix circuit 181.

After the high frequency components in accordance with the pass band included in the low-pass filter 143 are cut, and after being synchronized by a synchronization circuit 144, the color difference signal outputted from the Y/C separation circuit 137 to the low-pass filter 143 is inputted to the first matrix circuit 181.

The low-pass filter 143 is configured to be able to change pass band characteristics in accordance with the observation mode, based on the observation mode switching signal outputted from the control circuit 115.

Specifically, based on the observation mode switching signal outputted from the control circuit 115, the low-pass filter 143 passes only a band further lower than the low-pass filter 141 in the normal observation mode and passes a band substantially the same as the low-pass filter 141 in the narrow band imaging mode.

Based on the luminance signal outputted from the low-pass filter 141 and the color difference signal outputted from the synchronization circuit 144, the first matrix circuit 181 uses, for example, a 3 by 3 matrix to execute a color conversion for converting the luminance signal and the color difference signal to an RGB signal having R, G, and B components and then outputs the KGB signal to the γ correction circuit 182.

The γ correction circuit 182 executes γ-correction to the RGB signal outputted from the first matrix circuit 181 so that the contrast on the low signal level side is enhanced and then outputs the RGB signal after the γ-correction to the second matrix circuit 183.

Based on the RGB signal outputted from the γ correction circuit 182, the second matrix circuit 183 uses, for example, a 3 by 3 matrix to execute a process for converting the RGB signal to the luminance signal and the color difference signal, and then outputs the luminance signal to the selector 139 and outputs the color difference signal to an enlargement circuit 147.

Based on the observation mode switching signal outputted from the control circuit 115, the selector 139 outputs the luminance signal outputted from the γ correction circuit 138 to the enlargement circuit 147 in the normal observation mode, and outputs the luminance signal outputted from the second matrix circuit 183 to the enlargement circuit 147 in the narrow band imaging mode.

The luminance signal outputted from the selector 139 is subjected to an enlargement process by the enlargement circuit 147, subjected to an edge enhancement by the enhancement circuit 148, and then inputted to a third matrix circuit 149. The color difference signal outputted from the second matrix circuit 183 is subjected to the enlargement process by the enlargement circuit 147 and then inputted to the third matrix circuit 149.

The third matrix circuit 149 generates a video signal based on the luminance signal outputted from the enhancement circuit 148 and the color difference signal outputted from the enlargement circuit 147 and then outputs the video signal to D/A conversion circuits 184a, 184b, and 184c.

The D/A conversion circuits 184a, 184b, and 184c respectively store R, G, and B components included in the video signal outputted from the third matrix circuit 149, convert the stored components to analog, and then output the components to the monitor 105 as an analog video signal.

An action of the endoscopic device 101 of the present embodiment will now be described.

An operator or the like first brings the endoscopic device 101 into the initial state as shown in FIG. 10 by connecting the endoscope 102 to the light source device 103 and the video processor 104 and by applying power to the above components and the monitor 105. The endoscopic device 101 is set to the normal observation mode in the initial state.

In the normal observation mode, the control circuit 115 outputs an observation mode switching signal to the filter insertion/removal mechanism 116 to remove the narrow band imaging filter 124 from the optical path of the lamp 120. With the narrow band imaging filter 124 being removed from the optical path of the lamp 120, the light source device 103 emits illumination light for normal observation. The illumination light for normal observation emitted from the light source device 103 is transmitted by the light guide 113 and emitted to the subject through the illumination lens 127.

The CCD 129 picks up an image of the subject illuminated by the illumination light for normal observation and image-formed by the objective lens 128 and then outputs the picked up image of the subject to the video processor 104 as an image pickup signal.

The video processor 104 applies the processes to the image pickup signal outputted from the CCD 129 to generate a video signal in the above components and outputs the video signal to the monitor 105. In this way, the image of the subject in the normal observation is displayed on the monitor 105. More specifically, in the normal observation mode, after execution of the processes such as correlated double sampling and A/D conversion, the image pickup signal outputted from the AGC circuit 152 is converted to a luminance signal and a color difference signal in the Y/C separation circuit 137. After execution of a γ correction process, the luminance signal outputted from the Y/C separation circuit 137 is inputted to the enlargement circuit 147 through the selector 139, subjected to an enlargement process and an enhancement process, and then converted to an analog video signal and outputted to the monitor 105.

The color difference signal outputted from the Y/C separation circuit 137 is inputted to and synchronized by the synchronization circuit 144 through the low-pass filter 143. The color difference signal is subjected to a color conversion process, a γ correction process, and an enlargement process and then converted to an analog video signal and outputted to the monitor 105.

With the image of the subject in the normal observation being displayed on the monitor 105, based on the brightness signal outputted from the brightness detection circuit 135, the light control circuit 136 outputs a brightness control signal to the aperture drive circuit 123 to thereby control the aperture device 122 for increasing the amount of opening when detecting that the image is not displayed as an image with a desired brightness suitable for the normal observation. The aperture drive circuit 123 then increases the amount of opening of the aperture device 122 based on the brightness control signal outputted from the light control circuit 136.

Subsequently, based on the brightness signal outputted from the brightness detection circuit 135, the light control circuit 136 outputs a control switching signal to the control circuit 115 when detecting that the image of the subject displayed on the monitor 5 is not displayed as an image with a desired brightness suitable for normal observation even when the aperture device 122 has fully opened the aperture.

Based on the control switching signal outputted from the light control circuit 136, the control circuit 115 outputs a brightness control signal to the AGC circuit 152 to execute a control to the AGC circuit 152 for amplifying the signal level of the image pickup signal to a predetermined signal level.

As the control circuit 115 and the light control circuit 136 execute the control processes, an image of the subject having a desired brightness suitable for normal observation is displayed on the monitor 105.

In the normal observation, for example, the control circuit 115 controls the lamp drive circuit 170 to maintain the drive current of the lamp 120 as the first drive current.

Subsequently, once the operator or the like operates the mode changing switch 114 to output a switching instruction signal for switching the observation mode of the endoscopic device 101 from the normal observation mode to the narrow band imaging mode to the processor 104, the control circuit 115 outputs the observation mode switching signal to the filter insertion/removal mechanism 116, the CCD driver 131, the Y/C separation circuit 137, the selector 139, the low-pass filter 143, the enhancement circuit 148, the first matrix circuit 181, the γ correction circuit 182, and the second matrix circuit 183.

The control circuit 115 outputs the observation mode switch signal to the filter insertion/removal mechanism 116 to thereby arrange the narrow band imaging filter 124 on the optical path of the lamp 120. The control circuit 115 outputs the observation mode switching signal to the CCD driver 131 to thereby control the CCD driver 131 so that the CCD 129 is brought into the driving state suitable for the narrow band imaging mode. The control circuit 115 outputs the observation mode switching signal to the Y/C separation circuit 137, the selector 139, the low-pass filter 143, the enhancement circuit 148, the first matrix circuit 181, the γ correction circuit 182, and the second matrix circuit 183 to thereby control the above components so that the processes in the narrow band imaging mode are executed. With the execution of the controls, the observation mode of the endoscopic device 101 is switched from the normal observation mode to the narrow band imaging mode (step S11 of FIG. 12).

With the narrow band imaging filter 124 being arranged on the optical path of the lamp 120, the light source device 103 emits the illumination light for narrow band imaging. The illumination light for narrow band imaging emitted from the light source device 103 is transmitted by the light guide 113 and then emitted to the subject through the illumination lens 127.

Meanwhile, the CCD 129 picks up the image of the subject illuminated by the illumination light for narrow band imaging and further image-formed by the objective lens 128 and then outputs the picked up image of the subject to the video processor 104 as an image pickup signal.

The video processor 104 applies the processes to the image pickup signal outputted from the CCD 129 in the above components to generate a video signal and outputs the video signal to the monitor 105. In this way, the image of the subject in the narrow band imaging is displayed on the monitor 105. More specifically, in the narrow band imaging mode, after execution of the processes such as correlated double sampling and A/D conversion, the image pickup signal outputted from the AGC circuit 152 is converted to a luminance signal and a color difference signal in the Y/C separation circuit 137. The luminance signal outputted from the Y/C separation circuit 137 is inputted to the first matrix circuit 181 through the low-pass filter 141 and subjected to a color conversion process as well as a γ correction process in the first matrix circuit 181, the γ correction circuit 182, and the second matrix circuit 183. The luminance signal is then inputted to the enlargement circuit 147 through the selector 139, subjected to an enlargement process and an enhancement process, converted to an analog video signal, and outputted to the monitor 105.

The color difference signal outputted from the Y/C separation circuit 137 is inputted to and synchronized by the synchronization circuit 144 through the low-pass filter 143, subjected to a color conversion process and a γ correction process in the first matrix circuit 181, the γ correction circuit 182, and the second matrix circuit 183, subjected to an enlargement process in the enlargement circuit 147, further converted to an analog video signal, and then outputted to the monitor 105.

With the image of the subject in the narrow band imaging being displayed on the monitor 105, when the light control circuit 136 detects that the image is not displayed as an image with a desired brightness suitable for the narrow band imaging based on the brightness signal outputted from the brightness detection circuit 135 (step S12 of FIG. 12), the light control circuit 136 outputs a brightness control signal to the aperture drive circuit 123 to execute a control for increasing the amount of opening of the aperture device 122. Based on the brightness control signal outputted from the light control circuit 136, the aperture drive circuit 123 increases the amount of opening of the aperture device 122 (step S13 of FIG. 12).

Subsequently, based on the brightness signal outputted from the brightness detection circuit 135, when the light control circuit 136 detects that the image of the subject displayed on the monitor 105 is not displayed as an image with a desired brightness suitable for the narrow band light even when the aperture device 122 has fully opened the aperture (step S14 of FIG. 12), the light control circuit 136 outputs a control switching signal to the control circuit 115.

Based on the control switching signal outputted from the light control circuit 136, the control circuit 115 outputs the brightness control signal to the lamp drive circuit 170 to execute a control for increasing the drive current of the lamp 120, for example, from the second drive current to the third drive current, which is a driver current higher than the second drive current (step S15 of FIG. 12). Based on the brightness control signal outputted from the control circuit 115, the lamp drive circuit 170 increases the drive current to be supplied to the lamp 120, for example, from the second drive current to the third drive current.

Subsequently, based on the brightness signal outputted from the brightness detection circuit 135, when the light control circuit 136 detects that the image of the subject displayed on the monitor 105 is not displayed as an image with a desired brightness suitable for the narrow band light even when the aperture device 122 has fully opened the aperture and the drive current supplied to the lamp 120 is increased to the third drive current (step S16 of FIG. 12), the light control circuit 136 outputs a control switching signal to the control circuit 115.

Based on the control switching signal outputted from the light control circuit 136, the control circuit 115 outputs the brightness control signal to the AGC circuit 152 to execute a control to the AGC circuit 152 for amplifying the signal level of the image pickup signal to a predetermined signal level (step S17 of FIG. 12).

The series of controls described above, i.e., the control to the aperture drive circuit 123 for increasing the amount of opening of the aperture device 122, the control to the lamp drive circuit 170 for changing the drive current supplied to the lamp 120 in stages, and the control to the AGC circuit 152 for amplifying the signal level of the image pickup signal are executed by the endoscopic device 101 in the narrow band imaging mode in the above order to thereby display on the monitor 105 an image with as little reduction of S/N as possible and a desired brightness suitable for observation.

In the endoscopic device 1 and the endoscopic device 101 of the present embodiment, various modifications to the configurations can be made without departing from the scope of the invention.

It is obvious that the present invention is not limited to the embodiments described above, and various modifications and applications can be made without departing from the scope of the invention.

What is claimed is:

1. An endoscopic device comprising:
an endoscope comprising an image pickup unit for picking up an image of a subject and outputting the picked up image of the subject as an image pickup signal;
an image pickup signal amplification unit for amplifying the image pickup signal;
a light source unit for emitting first illumination light having at least a visible region band to the subject;
a light intensity control unit for controlling an amount of light emitted from the light source unit, the light intensity control unit comprising:
  a diaphragm arranged on an optical path of the light source unit; and
  a light source drive unit that supplies a drive current to the light source unit;
a spectral unit, having predetermined spectral characteristics, for penetrating a light in a band based on the predetermined spectral characteristics among the lights emitted from the light source unit when arranged on the optical path of the light source unit;
a brightness control unit for controlling a brightness of an image generated based on the image pickup signal and displayed on a display unit; and
a mode switching unit for switching a first mode in which the spectral unit is removed from the optical path of the light source unit to emit the first illumination light to the subject and a second mode in which the spectral unit is arranged on the optical path of the light source unit to emit the second illumination light having a band narrower than the first illumination light to the subject,
wherein the brightness control unit, in the second mode,
  controls the diaphragm when first detecting that the brightness of the image displayed on the display unit is not a brightness appropriate for observation,
  controls the light source drive unit when detecting that the brightness of the image displayed on the display unit is not a brightness appropriate for observation after an amount of an opening of the diaphragm has reached a maximum, and
  controls the image pickup signal amplification unit when detecting that the brightness of the image displayed on the display unit is not a brightness appropriate for observation after the amount of the opening of the diaphragm has reached the maximum and the drive current supplied from the light source drive unit to the light source unit has reached a predetermined upper limit value.

2. The endoscopic device according to claim 1, wherein the brightness control unit further
controls, in the first mode, the light source drive unit so as to maintain constant the drive current supplied to the light source unit, controls the diaphragm when first detecting that the brightness of the image displayed on the display unit is not a brightness appropriate for observation, and controls the light source drive unit when detecting that the brightness of the image displayed on the display unit is not a brightness appropriate for observation after the amount of the opening of the diaphragm has reached the maximum.

3. The endoscopic device according to claim 1, wherein the brightness control unit detects the brightness of the image generated based on the image pickup signal and executes a control to the light source drive unit for increasing the drive current supplied to the light source unit to the predetermined upper limit value in stages based on the detection result in the second mode.

4. The endoscopic device according to claim 1, wherein the brightness control unit, in the first mode, controls the image pickup signal amplification unit after executing a control to the diaphragm based on the brightness of the image displayed on the display unit, and in the second mode, increases the drive current supplied to the light source unit to be higher than the drive current in the first mode.

\* \* \* \* \*